United States Patent [19]

Sutter

[11] Patent Number: 4,461,297

[45] Date of Patent: Jul. 24, 1984

[54] FORCEPS

[75] Inventor: Hermann Sutter, Gundelfingen-Wildtal, Fed. Rep. of Germany

[73] Assignee: Holzhaur und Sutter Medizin-technische Gerate und Instrumente GmbH, Freiburg, Fed. Rep. of Germany

[21] Appl. No.: 359,429

[22] Filed: Mar. 18, 1982

[30] Foreign Application Priority Data

Mar. 19, 1981 [DE] Fed. Rep. of Germany ....... 3110666

[51] Int. Cl.³ .............................................. A61B 17/28
[52] U.S. Cl. ....................................... 128/321; 81/43; 128/354
[58] Field of Search ..................... 128/303 R, 321–326, 128/340, 346, 354–355; 81/43; 294/16

[56] References Cited

U.S. PATENT DOCUMENTS

| | | | |
|---|---|---|---|
| 1,889,475 | 11/1932 | Henkel | 128/354 X |
| 2,685,880 | 8/1954 | Curutchet | 81/43 X |
| 3,392,727 | 7/1968 | Hanlon | 128/354 X |
| 3,653,389 | 4/1972 | Shannon | 128/354 |
| 3,972,333 | 8/1976 | Leveen | 128/354 X |
| 3,977,410 | 8/1976 | Huston et al. | 128/354 |
| 4,318,313 | 3/1982 | Tartaglia | 128/354 X |

Primary Examiner—Dalton L. Truluck
Attorney, Agent, or Firm—Peter K. Kontler

[57] ABSTRACT

A forceps has legs which are connected to each other at the first of their ends and are movable toward and away from each other with their second ends in response to the application of pressure against their intermediate portions to thereby flex the legs in the region of the first ends. One of the legs carries a pin which extends into and is guided by a tubular component on the other leg so as to ensure that the legs are held against stray movements during each and every stage of their movement between open and closed positions. The tubular component cooperates with the one leg to determine the closed positions, and such component cooperates with the pin to determine the open positions, of the legs. The pin and the tubular component are disposed within the confines of and between the intermediate portions of the two legs in a region which is remote from the second ends and close to those parts of the intermediate portions which serve as handgrip means. A stop is provided between the tubular component and the first ends of the legs to prevent movements of the second ends away from each other in response to the application of pressure against the handgrip means in closed positions of the legs.

37 Claims, 6 Drawing Figures

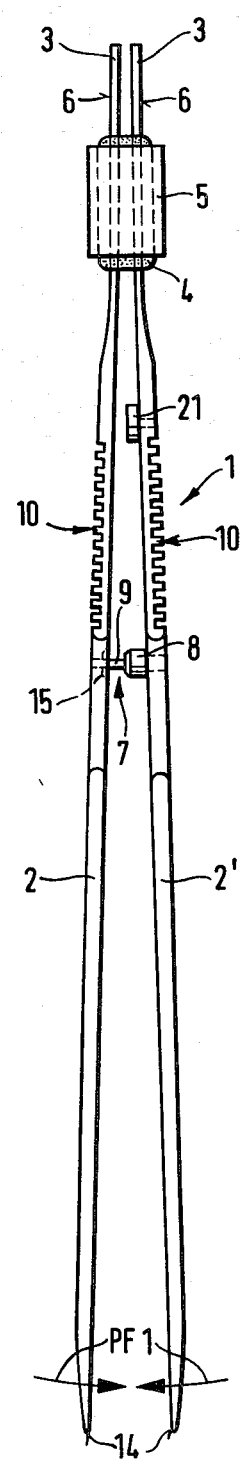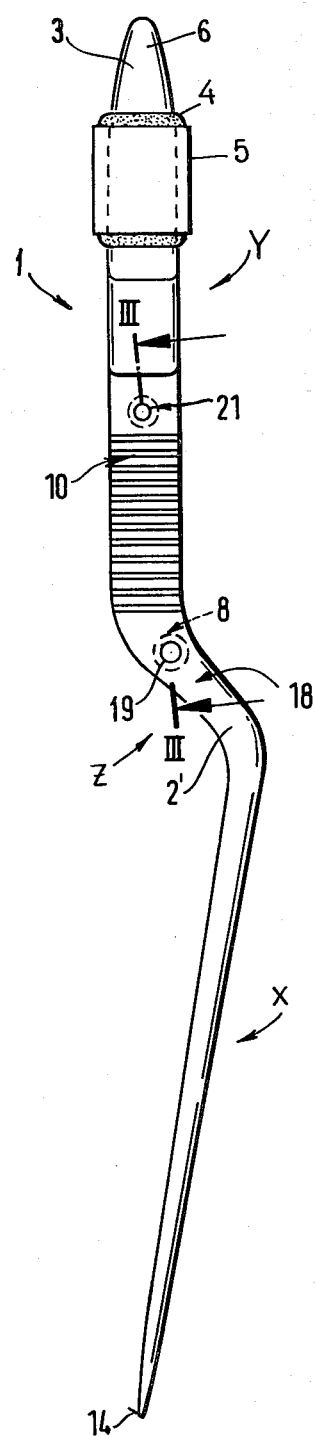

FORCEPS

BACKGROUND OF THE INVENTION

The present invention relates to pincers, tweezers, forceps and analogous instruments in general, and more particularly to improvements in instruments which are especially suited for use by surgeons (particularly for use in microsurgery) or for analogous purposes. Still more particularly, the invention relates to improvements in forceps-like or analogous instruments with two elongated legs and with means for guiding the legs during movement to their closed positions and/or for determining the closed positions.

It is already known to provide the legs of pincers, tweezers, forceps or analogous instruments (hereinafter called instruments for short) with guide means which ensure that the tips or working ends of the legs engage each other in closed positions of the legs and which start to guide the legs once the legs complete a certain movement from their fully open or spaced-apart positions. Such guide means serve to prevent tilting, shifting, jamming and/or other undesirable stray movements of the legs, for example, movements which would result in one of the tips bypassing the other tip in fully closed positions of the legs. A drawback of such conventional guide means is that they cannot invariably ensure proper guidance of the one and/or the other leg during each and every stage of movement of the tips of the two legs toward or away from each other. For example, twisting or analogous forces acting upon one or both legs during the initial stage of movement of the two legs to their closed positions (namely, during that stage when the conventional guide means is not as yet in action) can entail such deformation of one or both legs that the guide means cannot become effective at all and the tip of one of the legs bypasses the tip of the other leg during the last stage of movement of the legs to closed positions. Such pronounced deformation of one or both legs can result in total inability of the working ends or tips of the legs from moving into actual engagement with one another. A surgeon's work, e.g., in the course of complex brain surgery, is greatly impeded by any misalignment of the legs of a forceps, and the misaligned tips of the two legs can cause damage to tissue or to other substances or body parts of the patient.

OBJECTS AND SUMMARY OF THE INVENTION

An object of the invention is to provide an instrument of the above outlined character which is constructed and assembled in such a way that any misalignment of the two legs is not only highly unlikely but plain impossible, at least in the majority of cases.

Another object of the invention is to provide an instrument wherein the means for guiding the legs during movement between open and closed positions is constructed, assembled and configurated in a novel and improved way.

A further object of the invention is to provide the instrument with novel and improved means for determining the extent of movement of the legs between their open and closed positions, or at least the extent of movement to one of these positions.

An additional object of the invention is to provide the instrument with novel and improved means for centering the working ends of the legs, at least during the last stage of their movement into engagement with one another.

Another object of the invention is to provide a novel and improved instrument which is constructed and assembled with a view to reduce the likelihood of or to preclude improper manipulation and which, even though especially suited for use by surgeons (particularly but not exclusively by microsurgeons), can be put to a number of additional important and advantageous uses.

A further object of the invention is to provide the instrument with novel and improved means for preventing separation of the tips of the legs in response to the application of excessive forces in closed positions of the legs.

Another object of the invention is to provide a very simple instrument wherein the guide means for the legs can perform one or more additional important, advantageous and desirable functions.

Still another object of the invention is to provide an instrument wherein the stop means for determining the open or closed positions of the legs can perform one or more additional important, desirable and advantageous functions.

A further object of the invention is to provide an instrument which allows for smooth, gradual and gentle opening or closing of the legs and is thus less likely to cause injury or pain to a patient when the instrument is manipulated by a physician, dentist or nurse.

The invention is embodied in an instrument, particularly a forceps, for use by dentists, surgeons, general practitioners and/or other members of the medical profession. The instrument comprises first and second elongated legs having tips or end portions and interconnected second portions which are remote from the end portions. At least the first leg of the instrument is movable relative to the second leg between an open position in which the two end portions are spaced apart from and a closed position in which the two end portions are at least closely adjacent to each other. The instrument further comprises guide means for guiding the legs during each stage of movement of the first leg between its open and closed positions. The guide means is preferably disposed between the end portions and the second portions of the two legs. The legs normally include serrated, ribbed or otherwise roughened handgrip portions which are preferably located between the second portions and the guide means, i.e., the guide means is located between such handgrip portions and the end portions of the legs.

The instrument preferably further comprises stop means for preventing movements of the first leg beyond its open position. In accordance with a presently preferred embodiment of the invention, such stop means can form part of the guide means so that the latter performs several functions with attendant simplification of the instrument.

The legs are elongated and, in the open position of the first leg, such legs preferably slope toward each other in a direction from the end portions to the second portions. The intermediate portions of the legs between the end portions and the second portions are preferably spaced apart from each other in each position of the first leg, and the guide means is preferably constructed and/or mounted in such a way that it is disposed exclusively between and within the confines of the intermediate portions of the legs in each position of the first leg, i.e., such guide means can extend into the one and/or the other leg but it should not project outwardly so that it could injure the hand of the user and/or a patient. The aforementioned handgrip portions can constitute component parts of the intermediate portions of the legs and, as stated above, such handgrip portions are preferably disposed between the guide means and the second portions of the legs.

While it is not absolutely necessary that the guide means be disposed exclusively between and within the confines of the two legs, such situation preferably prevails at least while the first leg assumes its closed position.

The guide means preferably comprises a first member on one of the legs and a second member provided on the other leg and cooperating with the first member to hold the legs against stray movements during each and every stage of movement of the first leg between its open and closed positions. The first member is preferably a male guide member (such as an elongated pin-shaped component), and the second member is preferably a female member (such as a tubular component) designed for reception of a portion of the elongated pin-shaped component in each and every position of the first leg. The tubular component can include means for preventing movements of the first leg beyond the closed position. The arrangement is such that the tubular component is spaced apart from the one leg in the open position of the first leg and the length of the pin-shaped component exceeds the distance between the tubular component and the one leg (in the open position of the first leg) so that a portion of the pin-shaped component extends into the tubular component in each and every position of the first leg. In the closed position of the first leg, the tubular component preferably abuts against a surface which forms part of the one leg and is spaced apart from and faces the tubular component in the open position of the first leg. At least the first leg of the instrument is preferably elastic and tends to assume its open position so that it must undergo deformation for movement to the closed position; the legs are preferably spaced apart in the region of the guide means, also in the closed position of the first leg, and the tubular component abuts against the one leg in the closed position of the first leg. The length of the exposed part of the tubular component at least approximates the distance between the two legs in closed position of the first leg.

In order to properly secure the tubular component to the other leg of the instrument, such tubular component preferably comprises a portion which extends into the other leg; such portion of the tubular component is preferably of reduced diameter (i.e., its diameter is less than the diameter of the remainder of the tubular component), and the other leg has a bore for the smaller-diameter portion of the tubular component. The just mentioned bore can be tapped, and the smaller-diameter portion of the tubular component is then formed with external threads mating with the threads in the tapped bore of the other leg. Alternatively, the smaller-diameter portion of the tubular component can be a press fit in the bore of the other leg. The axial length of the bore in the other leg preferably at least matches but can exceed the length of the smaller-diameter portion of the tubular component so that the latter does not extend outwardly beyond the other leg.

In accordance with a further feature of the invention, the two components of the guide means can be provided with cooperating surfaces which prevent complete extraction of the pin-shaped component from the tubular component and thus determine the open position of the first leg. Such surfaces can include an internal shoulder in the tubular component and an external shoulder on the pin-shaped component. For example, the tubular component can be formed with an elongated axial passage having a smaller-diameter portion nearer to and a larger-diameter portion more distant from the one leg, and the internal shoulder is provided between such portions of the passage in the tubular component; the pin-shaped component then includes a plunger or piston which is reciprocable in the larger-diameter portion of the passage and a piston rod which is reciprocable in the smaller-diameter portion of the passage and is secured to or made integral with the one leg. The external shoulder is then provided on the piston and the latter is preferably snugly but slidably received in the larger-diameter portion of the passage in the tubular component to ensure accurate guidance of the first leg during movement between open and closed positions, i.e., while the peripheral surface of the piston slides along that internal surface of the tubular component which surrounds the larger-diameter portion of its passage.

As mentioned above, the entire guide means is preferably confined between and in the two legs of the instrument. Thus, the two components can be disposed between the two legs intermediate the end portions and the second portions of the legs. The one leg can have a first surface against which the tubular component abuts in closed position of the first leg and the other leg has a second surface facing away from the one leg. The distance between the first surface and the tubular component in the open position of the first leg at most equals the distance between the pin-shaped component and the second surface so that the pin-shaped component does not extend beyond the second surface in the closed position of the first leg.

The one leg can be formed with a recess facing the tubular component and receiving a portion of the tubular component in the closed position of the first leg. A surface in such recess can abut against the tubular component in the closed position of the first leg so that the one leg and the tubular component cooperate to prevent the first leg from moving beyond the closed position. The depth of the recess can approximate or equal one-half the thickness of the one leg, as considered in the axial direction of the tubular component of the guide means.

The one leg and the tubular component of the guide means can further comprise means for centering the tubular component relative to the one leg, at least in the closed position of the first leg and during the last stage of movement of the first leg to its closed position. Such centering means can include a chamfered or conical (e.g., frustoconical) end portion of the tubular component and a complementary recess in the inner side of the one leg, e.g., the aforementioned recess into which a portion of the tubular component extends in the closed position of the first leg.

At least one component (preferably the pin-shaped component) of the guide means preferably consists of a metallic material, and the other component may constitute an electrical insulator consisting of a suitable synthetic plastic material.

The instrument can comprise additional stop means for the first leg, preferably between the guide means and the second portions of the legs. This ensures that the first leg cannot be deformed beyond that condition in which the two end portions are immediately adjacent to or abut against each other, i.e., that the instrument cannot spread apart in the region of the end portions of its legs in response to an attempt to continue to deform the first leg while the latter assumes the prescribed closed position. Such additional stop means can constitute a synthetic plastic block which is secured to the first or to the second leg, preferably in the region of handgrip portions provided on the two legs intermediate the guide means and the second portions of such legs. The stop means preferably constitutes an electrical insulator.

The two legs of the instrument need not be straight. For example, each of the legs can comprise mutually inclined elongated first and second sections (one of which includes the respective end portion and the other of which includes the respective second portion) and a third section which connects the first and second sections to one another. The guide means is preferably disposed between and its components are preferably secured to the third sections of the two legs.

The novel features which are considered as characteristic of the invention are set forth in particular in the appended claims. The improved instrument itself, however, both as to its construction and the mode of using the same, together with additional features and advantages thereof, will be best understood upon perusal of the following detailed description of certain specific embodiments with reference to the accompanying drawing.

BRIEF DESCRIPTION OF THE DRAWING

FIG. 1 is an end elevational view of an instrument which embodies one form of the invention;

FIG. 2 is a side elevational view of the instrument;

DESCRIPTION OF THE PREFERRED EMBODIMENTS

Figure 3:
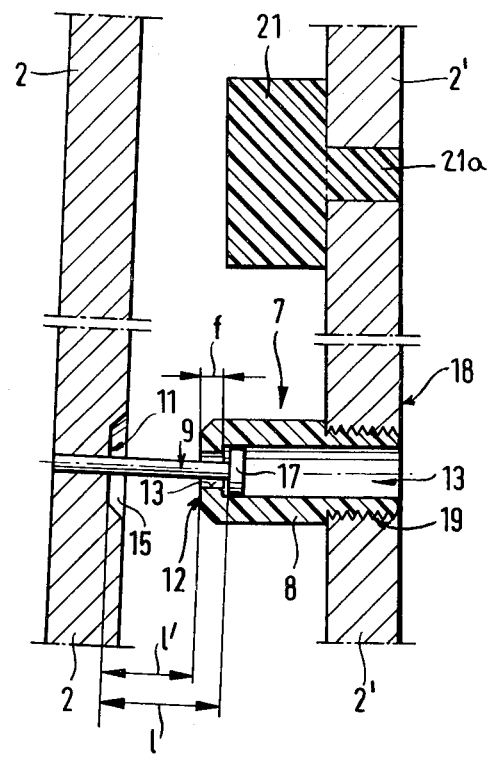
FIG. 3 is an enlarged fragmentary sectional view as seen in the direction of arrows from the line III—III of FIG. 2, showing the legs of the instrument in open positions.

Referring first to FIGS. 1 and 2, there is shown an instrument 1 which constitutes a coagulation forceps or a tweezers and includes two legs 2 and 2'. The legs 2, 2' include end portions or tips 14 which are spaced apart from each other when the instrument 1 is open, and second portions 3 which can constitute the second end portions of the respective legs and preferably also constitute electric terminals 6 for connection (if necessary) to a suitable energy source, not shown. The two legs are electrically insulated from each other and are secured to one another in the region of their second portions 3, such as by an insulating sleeve 4 which, in turn, is at least partially surrounded by a metallic sleeve or muff 5. The terminals 6 are flattened (note FIG. 1) and extend rearwardly beyond the connecting sleeves 4 and 5.

In accordance with a feature of the invention, the instrument 1 further comprises novel and improved guide means 7 which is disposed between and within the confines of the legs 2, 2' in the region between the end portions 14 and second portions 3 of the legs. The purpose of the guide means 7 is to prevent twisting or other stray movements of the leg 2 and/or 2' during opening or closing of the instrument 1, i.e., during movement of the leg 2 and/or 2' from an open position shown in FIG. 1 or 3 to a closed position (FIG. 4) in which the end portions 14 are immediately or closely adjacent to or actually touch each other, or vice versa. In other words, the guide means 7 is designed to be operative during each and every stage of movement of the leg 2 and/or 2' between its open and closed positions. The directions in which the end portions 14 move toward each other in response to movement of the legs 2 and 2' to closed positions are indicated by arrows Pfl shown in the lower part of FIG. 1. Such movements can be effected by deforming the legs 2 and 2' inwardly of the sleeves 4 and 5, i.e., by causing the major or intermediate portions of the two legs (including the externally ribbed, scored or otherwise roughened handgrip portions 10) to pivot in the region immediately below the sleeve 4, as viewed in FIG. 1. It will be noted that, when the legs 2 and 2' are in open positions, they slope toward each other in a direction from the end portions 14 toward the second portions 3. In fact, the legs 2 and 2' (with the possible exception of their end portions 14) remain spaced apart during each and every stage of their movement between open and closed positions. This provides room for exposed portions of the guide means 7 in the space between the intermediate portions of the two legs. FIG. 1 shows that the guide means 7 is disposed between the handgrip portions 10 and the end portions 14 and closer to the second portions 3 than to the end portions 14. The guide means 7 is especially effective in preventing stray movements of the legs 2 and 2' in directions forwardly of and behind the plane of FIG. 1, i.e., in substantial parallelism with the plane of FIG. 2.

Figure 4:
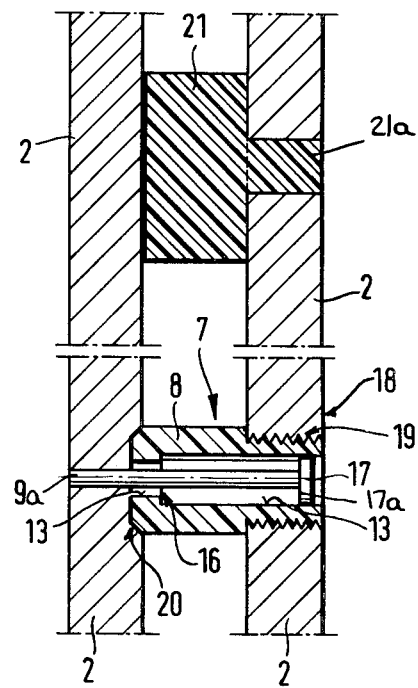
FIG. 4 is a sectional view similar to that of FIG. 3 but showing the legs of the instrument in closed positions.

In accordance with a presently preferred embodiment, the guide means 7 comprises an elongated pin-shaped male component 9 which is rigid with the left-hand leg 2, as viewed in FIGS. 1, 3 and 4, and an elongated female tubular component 8 which is rigid with the other leg 2' and into which at least a portion of the pin-shaped component 9 (hereinafter called pin for short) extends in each and every position of each of the two legs. This can be readily seen by comparing FIGS. 1 and 3 (showing the legs 2 and 2' in fully open positions) with FIG. 4 which shows the two legs in closed positions, namely, in positions in which the end portions 14 either contact or are closely adjacent to one another. FIGS. 3 and 4 further show that the entire guide means 7 is always disposed between and within the confines of the legs 2 and 2' irrespective of the positions of the two legs. This is desirable and advantageous in many instances, e.g., when the instrument is used as a forceps by a physician or a dentist, because the confinement of all parts of the guide means 7 in open, closed and intermediate positions of the two legs reduces the likelihood of accidental damage to tissue during an operation or another treatment of a patient.

As can be seen in FIG. 3, the distance l' between a surface 11 in a shallow recess 15 at the inner side of the leg 2 and the end face 12 of the tubular component 8 (hereinafter called tube) is less than the length l of the exposed portion of a piston rod 9a forming a smaller-diameter portion of the pin 9 and being permanently or detachably affixed to the leg 2 so as to extend beyond the surface 11 and toward and into the tube 8. The piston rod 9a carries a piston 17 which constitutes the end portion of the exposed part of the pin 9 and is slidably guided by a cylindrical internal surface bounding a larger-diameter portion of an axial passage 13 in the tube 8. The smaller-diameter portion of such passage receives a portion of the piston rod 9a with at least some clearance, and its diameter is less than that of the piston 17. The external shoulder or surface 17a between the piston rod 9a and piston 17 cooperates with an internal shoulder or surface 16 of the tube 8 to determine the open positions of the legs 2 and 2', i.e., to prevent the legs from moving beyond the open positions shown in FIGS. 1 and 3. The distance between the shoulder 16 and the end face 12 of the tube 8 is indicated at f. The distance l' is less than the distance between the exposed end face of the piston 17 and the surface 18 at the outer side of the leg 2'; this ensures that the piston 17 does not emerge from the larger-diameter portion of the passage 13 when the end face 12 abuts against the surface 11 in the recess 15, i.e., when the legs 2 and 2' assume their closed positions. Furthermore, and since the length l of the exposed part of the piston rod 9a exceeds the distance l' between the surface 11 and the end face 12 in open positions of the legs 2 and 2', a part of the exposed portion of the piston rod 9a necessarily extends into the tube 8 in each and every position of the leg 2 and/or 2'. When the legs 2 and 2' are moved to the closed positions shown in FIG. 4, the end face 12 abuts against the surface 11 in the recess 15 so that the tube 8 cooperates with the leg 2 to constitute a stop against movement of the leg 2 and/or 2' beyond the respective closed position. FIG. 4 further shows that the piston 17 then still remains in the larger-diameter portion of the passage 13 so that it cannot contact any tissue or other substance or the hand of the user when the legs 2 and 2' assume their closed positions. In addition, the internal surface of the tube 8 around the larger-diameter portion of the passage 13 invariably guides the peripheral surface of the piston 17 to thus ensure that there is no lateral wobbling of the legs 2 and 2' relative to each other during movement between the open and closed positions and/or in the open or closed positions of such parts. The length of the exposed part of the tube 8 in closed positions of the legs 2 and 2' equals the distance between the inner side of the leg 2' and the surface 11 in the recess 15 of the leg 2. The depth of the recess 15 is selected with a view to allow for a reasonable axial length (f) of the smaller-diameter portion of the passage 13 in the tube 8. The smaller-diameter portion of the passage 13 does but need not necessarily receive a part of the piston rod 9a with a certain amount of clearance, i.e., the piston rod 9a can be a sliding fit in such portion of the passage 13 to thereby further reduce the likelihood of stray movements of the legs 2 and 2' in the open, closed or any intermediate positions of such legs. The selection of configuration of the tube 8 in such a way that the distance f is rather pronounced is especially desirable when the piston rod 9a is a sliding fit in the smaller-diameter portion of the passage 13.

While the instrument 1 can be provided with discrete means for preventing movements of the legs 2 and 2' beyond the open positions of FIG. 4, the provision of such stop means or limiting means on the guide means 7 is particularly desirable and advantageous because there is no need for separate machining and/or for welding or other mode of connecting the separate stop means to the leg 2 and/or 2'. The stop means includes the aforementioned external surface or shoulder 17a between the piston 17 and piston rod 9a of the pin 9 and the internal shoulder 16 between the smaller- and larger-diameter portions of the passage 13 in the tube 8. As mentioned above, the distance between the exposed end face of the piston 17 and the external surface 18 of the leg 2' in open positions of the legs 2 and 2' exceeds or is not less than the distance l' to ensure that the piston 17 cannot extend beyond the surface 18 in closed positions of the legs.

The pin 9 preferably consists of a metallic material, and the tube 8 preferably consists of an electric insulating material, preferably a synthetic plastic insulating material. This ensures that the guide means 7 does not permit the flow of current between the legs 2 and 2'; the insulation is particularly desirable if the instrument is a coagulation forceps. Furthermore friction between a metallic and a plastic material (especially as a result of appropriate selection of the plastic material) is normally less than that between two metallic materials. This is desirable and advantageous because the movements of the legs 2 and 2' between their open and closed positions can be controlled with a much higher degree of accuracy, i.e., the legs are less likely to be abruptly moved to or from selected positions if an abrupt movement is not desired or is outright damaging.

The left-hand end portion of the pin 9 (as viewed in FIGS. 1, 3 and 4) can be a press fit in a complementary bore of the leg 2. The same holds true for the connection between the leg 2' and the smaller-diameter right-hand end portion 19 of the tube 8; however, and as shown in FIGS. 3 and 4, the smaller-diameter portion 19 of the tube 8 can be provided with external threads mating with the internal threads in a tapped bore of the leg 2'. This renders it possible to rapidly replace the tube 8 with a fresh tube. All that counts is to ensure that the portion 19 is securely anchored in the complementary bore of the leg 2' to thus ensure that the axial position of the tube 8 does not change when the instrument is in use. The material of the tube 8 should be sturdy enough to withstand stresses which arise when the legs 2 and 2' are moved to the closed positions of FIG. 4 in which the end face 12 bears against the surface 11 in the recess 15.

Figure 5:
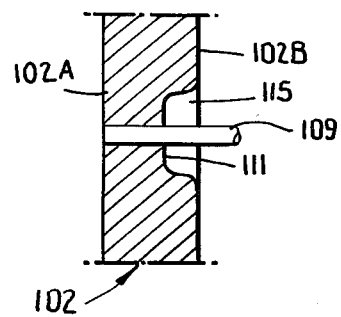
FIG. 5 is a fragmentary sectional view of one leg of a slightly modified instrument.

FIGS. 3 and 4 show that the recess 15 is relatively shallow. On the other hand, FIG. 5 shows a portion of a modified leg 102 having a deeper recess 115 so that the surface 111 at the bottom of this recess is located substantially midway between the outer surfaces 102A and 102B of the leg 102. The exact depth of the recess 15 or 115 will depend on the dimensions of the respective leg 2 or 102 and on the desired distance between the internal shoulder 16 of the tube 8 and the end face 12.

The tube 8 can be chamfered in the region (at 20) of the end face 12, and the configuration of the surface bounding the recess 15 can be complementary so that this recess is at least substantially filled by a portion of the tube 8 in the closed positions of the legs 2 and 2' (as shown in FIG. 4). In such instances, the chamfered portion 20 of the tube 8 cooperates with the surfaces bounding the recess 15 to center the pin 9 in the tube and to ensure predictable movement of the legs 2 and 2' to their closed positions as often as desired or necessary. In other words, the tube 8 can cooperate with the leg 2 to constitute therewith a centering means for the pin 9, at least during the last stage of movement of the leg 2 and/or 2' to its closed position.

Figure 6:
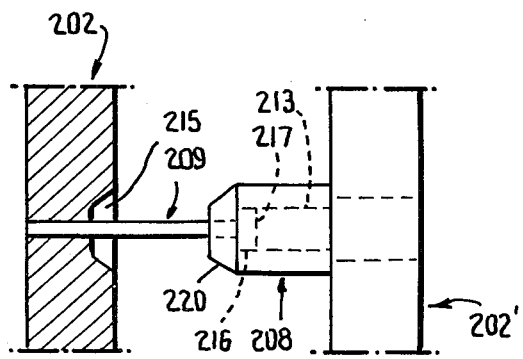
FIG. 6 is a fragmentary partly sectional and partly end elevational view of a third instrument.

FIG. 6 shows a portion of a third instrument wherein all such parts which are similar or clearly analogous to corresponding parts of the instrument of FIGS. 1 to 4 are denoted by similar reference characters plus 200. The chamfered portion 20 of FIGS. 1 to 4 is replaced with a frustoconical portion 220 which can be received in the complementary recess 215 of the leg 202 and even more accurately center the pin 209 relative to the tube 208. It goes without saying that the centering means can be configured in many other ways without departing from the spirit of the invention. For example, the conical portion 220 can be replaced with a substantially hemispherical portion which fits into a complementary recess or socket (bounded by a concave surface) in the inner side of the leg for the pin of the guide means.

Referring again to FIGS. 1 to 4, FIGS. 1, 3 and 4 show a further stop 21 which is interposed between the guide means 7 and the sleeves 4, 5 (and more specifically between the handgrip portions 10 and the second portions 3 of the legs 2, 2') and limits the extent of movement of the handgrip portions 10 toward each other during movement of the legs 2 and 2' to their closed positions. This stop preferably consists of a suitable synthetic plastic material and has a smaller-diameter portion 21a received in a complementary bore of the leg 2'. The main purpose of the stop 21 is to prevent excessive deformation of the leg 2 and/or 2' such as would cause the end portions 14 to move apart after the end face 12 of the tube 8 reaches the surface 11 in the recess 15 of the leg 2. However, the stop 21 can also replace the stop means of the guide means, i.e., the piston 17 of the pin 9 and the internal shoulder 16 of the tube 8.

FIG. 2 shows that each leg of the improved instrument 1 includes two elongated mutually inclined sections X and Y the former of which embodies the respective end portion 14 and the latter of which embodies the respective second portion 3, as well as a third section Z which connects the two mutually inclined sections with one another so that the legs 2 and 2' resemble distorted letters "Z". Such configuration is often desirable when the instrument 1 is used as a forceps. The guide means 7 is provided in the region of the sections Z, i.e., one of these sections carries the pin 9 and the other section Z carries the tube 8 of the guide means 7 shown in FIGS. 1 to 4.

An important advantage of the improved instrument is that its legs are guided during each stage of their movement between closed and open positions as well as that each leg is also held against stray movements in its open or closed position. Moreover, the guide means can serve to prevent movements of the legs beyond their open or closed positions, i.e., it can constitute a portion of or the entire means for preventing the legs from moving beyond their open or closed positions. Still further, the guide means is simple, compact and inexpensive, and it does not interfere with proper manipulation of the instrument; on the contrary, such guide means contributes to more reliable and predictable manipulation of the instrument by a dentist, surgeon or another person. The guide means can be embodied with equal advantage in tweezers for use by beauticians and for similar purposes. The user can release the handgrip portions 10 without the danger of allowing the components of the guide means to become separated from one another and/or of allowing twisting and/or other stray movements of the one and/or other leg. The stop 21 constitutes an optional but highly desirable and advantageous feature of the improved instrument; as shown, this stop is or can be positioned and mounted in such a way that it does not extend beyond the outlines of the legs except into the space between the legs, preferably in the region between the handgrip portions 10 and the second portions of the legs. The stop 21 is optional because, if the material of the legs is such that it is not likely to flex except where desired (such as in immediate proximity of the sleeve 4 where the thickness of each of the two legs is preferably reduced to enhance the flexibility of the legs in the region where they are connected to one another), the end portions 14 are not likely to move apart once the legs have assumed their closed positions while the user continues to exert pressure against the outer sides of the handgrip portions 10. The combination of the improved guide means with the stop 21 ensures that the legs of the instrument are held against any undesirable movements during each and every stage of movement of the two legs as well as in both end positions (i.e., open and closed positions) of the legs.

Prevention of excessive opening of the instrument (i.e., a movement of the one and/or other leg beyond its prescribed open position) is particularly undesirable under certain circumstances which arise, for example, in an operating room. Thus, when a surgeon uses the instrument for introduction of the end portions 14 into a narrow cavity of an animal body (such as during brain surgery), any movements of the end portions 14 of the instrument 1 shown in FIGS. 1 to 4 could cause serious damage to the tissue surrounding such cavity. By way of example, the distance between the end portions 14 in open positions of the legs 2 and 2' forming part of the instrument 1 shown in FIGS. 1 to 4 can be in the range of 10 millimeters. This distance is sufficiently small to enable the user to introduce the end portions 14 into or to withdraw such end portions from a relatively narrow cavity without exerting pressure against the handgrip portions 10 during introduction or withdrawal.

The guide means can be placed closer to the end portions 14 or to the second portions 3. As a rule, such guide means will be placed between the intermediate portions of the two legs at a location where the legs provide ample room for exposed portions of the components of the guide means in closed positions of the legs. Another consideration in selecting the position of the guide means is that such guide means can be readily mounted in the adjacent portions of the legs as well as that they are remote from those portions of the legs which are to engage a tissue or the like in actual use of the instrument. It has been found that the region of or close to the handgrip portions is quite satisfactory for mounting the components of the guide means. At the present time, it is preferred to locate the guide means immediately in front of the handgrip portions 10, i.e., between (but close to) the handgrip portions and the end portions 14 of the legs 2 and 2' shown in FIGS. 1 to 4. This ensures that the guide means is sufficiently remote from those portions of the legs which are used for engagement of tissue or the like in actual use of the instrument and that the guide means does not interfere with manipulation of the instrument by way of the handgrip portions 10.

Since the handgrip portions 10 are preferably placed between the guide means 7 and the stop 21, the end portions 14 are highly unlikely to move apart even if the user exerts a strong pressure against the handgrip portions in closed positions of the legs. The distance between the guide means 7 and the stop 21 is relatively small so that the handgrip portions 10 therebetween can stand pronounced flexing or bending stresses without permitting the end portions 14 to move away from one another while the end face 12 abuts against the surface 11 and the stop 21 abuts against the inner side of the leg 2.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A microsurgical forceps comprising:
   (a) a pair of elongated legs having end portions and interconnected second portions remote from said end portion, said legs having a closed position in which said end portions are at least closely adjacent to each other, and said legs being resiliently biased relative to each other to an open position in which said end portions are remote from one another, said legs assuming said open position in the absence of a force urging said legs to said closed position, and said legs together defining a clearance in all positions from said open position to said closed position; and
   (b) guide means in said clearance for guiding said legs in all positions from said open position to said closed position, said guide means being disposed entirely within the confines of and between said legs in all positions from said open position to said closed position, and said guide means including an elongated pin-shaped component on one of said legs, and a substantially circumferentially complete tubular component on the other of said legs, said components being disposed intermediate said end portions and said second portions of said legs, and said one leg having a recess which faces said tubular component and receives a portion thereof in said closed position to center said tubular component relative to said one leg, said one leg having a first surface against which said tubular component abuts in said closed position, and said other leg having a second surface facing away from said one leg, said tubular component being spaced apart from said first surface by a predetermined distance in said open position, and the length of said elongated component exceeding said predetermined distance so that a portion of said elongated component extends into said tubular component in all positions from said open position to said closed position, said predetermined distance being at most equal to the distance between said elongated component and said second surface so that said elongated component does not extend beyond said second surface in said closed position.

2. The forceps of claim 1, wherein said second portions comprise electrical terminals for connecting said legs to a current source and said legs are electrically insulated from one another.

3. The forceps of claim 1, wherein at least one of said legs is elastic and said legs are biased to said open position at least in part by the elasticity of said elastic leg.

4. The forceps of claim 3, wherein both of said legs are elastic and said legs are biased to said open position substantially entirely by the elasticity thereof.

5. The forceps of claim 1, wherein said legs further include handgrip portions disposed intermediate the end portions and the second portions thereof, said guide means being disposed between the handgrip portions and the end portions of said legs.

6. The forceps of claim 1, comprising stop means for preventing the movement of said legs beyond said open position.

7. The forceps of claim 6, wherein said stop means forms part of said guide means.

8. The forceps of claim 1, wherein said legs, in the open position, slope toward each other in a direction from the end portions toward the second portions thereof, said legs further including intermediate portions extending between said end portions and said second portions and being spaced apart from one another in the closed position.

9. The forceps of claim 8, wherein said guide means is disposed exclusively between and within the confines of said intermediate portions in each position of said legs.

10. The forceps of claim 9, wherein the intermediate portion of each of said legs includes a handgrip portion and said guide means is disposed between such handgrip portions and the end portions of said legs.

11. The forceps of claim 1, wherein said tubular component includes means for preventing movements of said legs beyond said closed position.

12. The forceps of claim 1, wherein a leg is elastic so that it must undergo deformation for movement to said closed position.

13. The forceps of claim 1, wherein said legs are spaced apart by a predetermined distance in the region of said guide means in the closed position and the length of said tubular component between said legs approximates such distance.

14. The forceps of claim 1, wherein said tubular component has a section extending into said other leg.

15. The forceps of claim 14, wherein said section of said tubular component has a diameter less than that of the remainder of said tubular component and said other leg has a bore for said section of said tubular component.

16. The forceps of claim 15, wherein said bore is tapped and said section of said tubular component has external threads mating with the threads in said bore.

17. The forceps of claim 15, wherein said section of said tubular component is a press fit in said bore.

18. The forceps of claim 15, wherein the axial length of said bore at least matches the axial length of said section of said tubular component so that such section of the tubular component does not extend beyond said other leg.

19. The forceps of claim 1, wherein said components have cooperating surfaces which prevent complete extraction of said elongated component from said tubular component and which determine the open position.

20. The forceps of claim 19, wherein said surfaces include an internal shoulder in said tubular component and an external shoulder on said elongated component.

21. The forceps of claim 20, wherein said tubular component has an elongated passage having a smaller-diameter portion nearer to and a larger-diameter portion more distant from said one leg, said internal shoulder being disposed between said portions of said passage and said elongated component including a piston reciprocable in the larger-diameter portion of said passage and a piston rod reciprocable in said smaller-diameter portion of said passage, said external shoulder being provided on said piston.

22. The forceps of claim 21, wherein said tubular component has an internal surface surrounding said larger-diameter portion of said passage and slidably guiding said piston during movement of said legs between said open and closed positions.

23. The forceps of claim 1, wherein said first surface is in said recess.

24. The forceps of claim 1, wherein said one leg has a predetermined thickness in the region of said recess, as considered in the longitudinal direction of said components, and the depth of said recess approximates or equals one-half said thickness.

25. The forceps of claim 1, wherein said tubular component and recess include complementary chamfered portion.

26. The forceps of claim 1, wherein said centering tubular component and recess include complementary conical portion.

27. The forceps of claim 1, wherein one of said components consists of a metallic material.

28. The forceps of claim 27, wherein the other of said components consists of a synthetic plastic material.

29. The forceps of claim 27, wherein the other of said components is an electrical insulator.

30. The forceps of claim 27, wherein said one component is said elongated pin-shaped component.

31. The forceps of claim 1, comprising stop means for holding said legs against movement beyond said closed position.

32. The forceps of claim 31, wherein said stop means is disposed between said guide means and the second portions of said legs.

33. The forceps of claim 32, wherein said stop means consists of synthetic plastic material.

34. The forceps of claim 32, wherein said stop means is an electrical insulator.

35. The forceps of claim 32, wherein at least one of said legs is deformable and said legs include handgrip portions disposed between said stop means and said guide means.

36. The forceps of claim 1, wherein each of said legs includes two elongated mutually inclined sections and a third section connecting said mutually inclined sections, said guide means being disposed between the third sections of said legs.

37. The forceps of claim 21, wherein said piston rod has a diameter approximating that of said smaller-diameter portion of said passage and said piston has a diameter approximating that of said larger-diameter portion of said passage.

* * * * *